(12) United States Patent
Sitruk-Ware et al.

(10) Patent No.: US 8,865,200 B2
(45) Date of Patent: Oct. 21, 2014

(54) SUSTAINED RELEASE COMPOSITIONS CONTAINING PROGESTERONE RECEPTOR MODULATORS

(75) Inventors: Regine Sitruk-Ware, New York, NY (US); Yun-Yen Tsong, North Caldwell, NJ (US)

(73) Assignee: Laboratoire HRA Pharma (FR)

( * ) Notice: Subject to any disclaimer, the term of this patent is extended or adjusted under 35 U.S.C. 154(b) by 1400 days.

(21) Appl. No.: 11/631,877

(22) PCT Filed: Jul. 8, 2005

(86) PCT No.: PCT/US2005/024474
§ 371 (c)(1),
(2), (4) Date: Jan. 15, 2008

(87) PCT Pub. No.: WO2006/010097
PCT Pub. Date: Jan. 26, 2006

(65) Prior Publication Data
US 2008/0199511 A1    Aug. 21, 2008

Related U.S. Application Data

(60) Provisional application No. 60/586,783, filed on Jul. 9, 2004.

(51) Int. Cl.
*A61F 6/06* (2006.01)
*A61K 31/56* (2006.01)
*A61K 47/30* (2006.01)
*A61K 47/24* (2006.01)
*A61K 9/00* (2006.01)
*A61F 6/08* (2006.01)

(52) U.S. Cl.
CPC . *A61F 6/08* (2013.01); *A61K 47/24* (2013.01); *A61K 9/0036* (2013.01)
USPC .......................... 424/430; 514/177; 514/772.3

(58) Field of Classification Search
USPC ................................ 424/430; 514/177, 772.3
See application file for complete search history.

(56) References Cited

U.S. PATENT DOCUMENTS

| | | | |
|---|---|---|---|
| 3,545,439 A * | 12/1970 | Duncan | 128/832 |
| 3,948,254 A | 4/1976 | Zaffaroni | |
| 5,211,952 A | 5/1993 | Spicer et al. | |
| 5,972,372 A | 10/1999 | Saleh et al. | |
| 6,126,958 A * | 10/2000 | Saleh et al. | 424/432 |
| 6,358,947 B1 * | 3/2002 | Zhi et al. | 514/229.5 |
| 6,861,415 B2 | 3/2005 | Kim et al. | |
| 2002/0025951 A1 * | 2/2002 | Kim et al. | 514/169 |
| 2002/0161352 A1 * | 10/2002 | Lin et al. | 604/515 |

FOREIGN PATENT DOCUMENTS

| | | |
|---|---|---|
| JP | 11-512965 T | 11/1999 |
| JP | 2000509396 A | 7/2000 |
| KR | 100161975 | 11/1998 |
| WO | 8912448 A1 | 12/1989 |
| WO | 97/41145 | 11/1997 |
| WO | WO 97/41145 * | 11/1997 |
| WO | 98/04220 A1 | 2/1998 |
| WO | 02074083 A1 | 9/2002 |
| WO | 2004/096151 A2 | 11/2004 |
| WO | WO 2004/096151 A2 * | 11/2004 |
| WO | 2006/017075 A1 | 2/2006 |

OTHER PUBLICATIONS

Sitruk et al. ("Nestorone:clinical applications for contraception and HRT" in Steroids, 68, Nov. 23, 2003, pp. 907-913 submitted by applicant of form 1449).*
Office Action from corresponding Columbian Application No. 07.012.095 issued Sep. 20, 2010.
Passaro, M. D. et al, Luteal phase dose-response relationships of the antiprogestin CDB-2914 in normally cycling women, Hum Reprod, 2003, vol. 18, No. 9, p. 1820-7.
Gainer, E. E. et al, Pharmacologic properties of CDB (VA)—2914, Steroids, 200 3, vol. 68, No. 10-13, p. 1005-11.
Office Action from corresponding Japanese Application No. 2007-520580, dated Oct. 25, 2010.
Sitruk-Ware et al., "Nestorone: Clinical applications for contraception and HRT", Steroids vol. 68, No. 10/13, Nov. 2003, pp. 907-913.
Project CDB-2914 Ring http://www.popcouncil.org/projects/BIO_CDB291 4Ring.html. Internet page updated on Jun. 29, 2005.
Sitruk-Ware, R., et al, "Nestorone: clinical applications for contraception and HRT"; Steroids, Elsevier Science Publishers, New York, NY,US; 68(10-13); 907-913. Nov. 2003.
European Search Report, EP 05 77 1439. Jun. 6, 2008.
Office Action from Corresponding Canadian Application 2573266, dated Dec. 8, 2009.

* cited by examiner

*Primary Examiner* — Blessing M Fubara
(74) *Attorney, Agent, or Firm* — Lerner, David, Littenberg, Krumholz & Mentlik, LLP (57) ABSTRACT

Disclosed are sustained release compositions for vaginal or transdermal administration that contain a progesterone receptor modulator such as CDB-2914 (also referred to as VA-2914), and methods of using them for long term contraception or therapeutic purposes. Also disclosed are methods for making the compositions.

18 Claims, 4 Drawing Sheets

FIG. 1A

FIG. 1B
THE SHADED AREAS ARE MICRONIZED
CDB-2914 IN SILICONE MATRIX

FIG. 2A

FIG. 2B
THE SHADED AREAS ARE MICRONIZED
CDB-2914 IN SILICONE MATRIX

IN VITRO RELEASE RATE OF CDB-2914

| TUBE | DIMENSIONS ODxID | MF (µg/day/ring) | CDB-2914 (µg/day/ring) |
|---|---|---|---|
| 18% EVA | 2.44 x 2.18mm | 0 | 96 |
| SILICONE TUBE C | 2.46 x 1.57mm | 48 | 160 |
| SILICONE TUBE D | 4.70 x 3.43mm | --- | 208 |
| SILICONE TUBE E | 6.96 x 6.35mm | --- | 512 |

IN VITRO RELEASE RATE vs SERUM LEVELS

| STEROID | IN VITRO (μg/day/ring) | SERUM LEVEL (pmol/L) |
|---|---|---|
| NESTORONE® | 50 | 120 |
| NESTORONE® | 75 | 200 |
| NESTORONE® | 150 | 280 |
| NESTORONE® | 200 | 400 |
| CDB-2914 | 400 | 3180 |

SUSTAINED RELEASE COMPOSITIONS CONTAINING PROGESTERONE RECEPTOR MODULATORS

CROSS-REFERENCE TO RELATED APPLICATIONS

The present application is a national phase entry under 35 U.S.C. §371 of International Application No. PCT/US2005/024474, filed Jul. 8, 2005, published in English, which claims benefit of U.S. Provisional Patent Application No. 60/586,783, filed Jul. 9, 2004. The disclosures of all of said applications are incorporated by reference herein.

BACKGROUND ART

In many therapeutic programs pertaining to the management of health and disease, the use of drug delivery devices that provide for the slow release of a drug to the body at a controlled rate over a prolonged period of time to achieve a desired physiologic or pharmacological effect has proved beneficial. A principal advantage of employing sustained-release compositions is that many therapeutic agents would otherwise be rapidly metabolized or cleared from the patient's system necessitating frequent administration of the drug to maintain a therapeutically effective concentration.

There has been a consistently large demand for the development of new, long-acting contraceptives that require minimal medical guidance and compliance as compared to oral contraceptives. This is particularly the case in less developed countries where medical and family planning organizations are inadequate. Accordingly, several long-acting, sustained release contraceptive delivery systems, including implants, vaginal rings, and transdermal systems have been developed. For a review, see Sitruk-Ware, et al., Contemporary Clin. Gynecol. & Obstet. 2:287-98 (2002).

SUMMARY OF THE INVENTION

CDB-2914 is a progesterone receptor modulator (PRM) with antagonist properties (also known as an anti-progestin). CDB-2914 has been reported as useful as an emergency or post-coital oral contraceptive. Applicants have discovered that such PRM's e.g., CDB-2914, (also referred to herein as "VA-2914") can be contraceptively effective when vaginally or transdermally administered via a sustained-release formulation. Therefore, such PRMs can be effectively used as a long term contraceptive, as well as for various therapeutic indications where sustained-release would be beneficial. Accordingly, by the terms "contraception", "contraceptively effective" and "long term contraception", it is meant to exclude emergency or post-coital administration, or contraceptive methods that entail daily oral administration.

Accordingly, a first aspect of the present invention is directed to a vaginal ring composition comprising a synthetic polymeric material containing a progesterone receptor modulator, e.g., CDB-2914. The amount of the PRM contained in the ring allows for release of the PRM in an amount that will be therapeutically or contraceptively effective for a predetermined time. In preferred embodiments, the ring is configured such that the PRM e.g., CDB-2914, diffuses through at least one layer of a polymeric material comprising a silicone elastomer to reach the external environment (e.g., the vaginal mucosa). In other preferred embodiments, the vaginal ring contains an inert polymer core, a surrounding layer of a polymer having an effective amount of the PRM, e.g., CDB-2914, dispersed therein (so as to form a polymer matrix), and an outer polymer layer, wherein the polymer in the inert core, the drug-containing surrounding layer, and the outer layer may be the same or different. In more preferred embodiments, the PRM is CDB-2914 and the polymers in the core, the surrounding drug-containing layer and the outer layer are each contain or are made of silicone elastomers, and which may be the same or different. In yet other preferred embodiments, the vaginal ring is configured such that the PRM e.g., CDB-2914, is contained in a layer of a polymer matrix that surrounds an inert polymer core.

A second aspect of the present invention is directed to a non-vaginal ring sustained-release composition e.g., a vaginal or transdermal gel, a cream or foam, or a transdermal patch, containing that releases a therapeutically or contraceptively effective amount of the PRM, e.g., CDB-2914. In preferred embodiments, the composition is in the form of a vaginal gel.

Related aspects of the invention are directed to methods of using the sustained release compositions of the present invention for long-term contraception, by administering them vaginally or transdermally.

Yet other aspects of the present invention are directed to use of the sustained release compositions of the present invention for non-contraceptive, therapeutic purposes, e.g., to antagonize endogenous progesterone, induce menses, treat dysfunctional uterine bleeding, delay endometrial maturation for potential use in IVF, treat endometriosis, dysmenorrhea, meningiomas and endocrine hormone-dependent tumors, e.g., breast cancer, uterine fibroids, uterine endometrial proliferation, and to induce labor.

Further aspects of the present invention are directed to methods of making the sustained release compositions of the present invention.

The sustained-release compositions of the present invention have many advantages. Unlike injectables or subdermal implants, the present invention entails continuous use, yet is user controlled without the need for daily attention, and easily terminated. Intravaginal or transdermal absorption of the PRM avoids the hepatic first pass effect and requires a lower dose, because it is directly applied to and directly absorbed by the vaginal mucosa or skin. The compositions are estrogen-free, and are devoid of side effects attributable to estrogens. Use of the compositions of the present invention may further result in reduced menstrual bleeding and blood loss, and endometrial atrophy.

BEST MODE FOR CARRYING OUT THE INVENTION

Progesterone receptor modulators have been disclosed as mixed progesterone-agonists-antagonists, wherein one end of the biological scale is represented by progesterone and the synthetic progestins, and the opposite end represented by pure progesterone antagonists such as onapristone and K 230211. See, also Steroids, 65:543-44 (2000) (preface); Chwalisz, et al., Steroids 65:741-51 (2000); and Elger, et al., Steroids 65:713-23 (2000). PRMs of the present invention that possess lesser or minimal agonist activity are useful for contraception, as well as obstetrical indications, menstrual regulation and breast cancer therapy. PRMs that possess relatively far greater progestin-agonistic activity are more suitable for treatment of endometriosis and uterine myoma. Determinations of the relative amounts of agonist or antagonist properties may be conducted in accordance with known techniques. See, Elger, W. et al, supra, and WO 98/05679. The progesterone receptor modulator 17α-acetoxy-11β-(4-N,N-dimethylaminophenyl)-19-norpregna-4,9-diene-3,20-dione (CDB-2914) is a preferred active, e.g., contraceptive, agent for purposes of the present invention. One method for practical, large-scale synthesis of this compound is reported in Rao, et al., Steroids 65:395-400 (2000). CDB-2914 may also be prepared in accordance with synthetic schemes disclosed in U.S. Pat. No. 4,954,490. Other progesterone receptor modulators useful in the present invention are CDB-2914 metabolites, such as monodemethylated CDB-2914 and didemethylated CDB-2914. Other PRMs are disclosed in U.S. Pat. No. 4,954,490 (i.e., 11β-aryl-19-norprogesterone analogs in which the 17β position is substituted by an acetyl group) (and which includes CDB-2914).

Yet other PRMs suitable for use in the present invention include 21-substituted progesterone analogs disclosed in WO 97/41145 (also U.S. Publication no. 20020025951 A1). The compounds have the general formula:

In Formula I, $R^1$ is a functional group including, but not limited to, —OCH$_3$, —SCH$_3$, —N(CH$_3$)$_2$, —NHCH$_3$, —CHO, —COCH$_3$ and —CHOHCH$_3$. $R^2$ is a functional group including, but not limited to, halogen, alkyl, acyl, hydroxy, alkoxy, acyloxy, alkyl carbonate, cypionyloxy, S-alkyl and S-acyl. $R^3$ is a functional group including, but not limited to, alkyl, hydroxy, alkoxy and acyloxy. $R^4$ is a functional group including, but not limited to, hydrogen and alkyl. Finally, X is a functional group including, but not limited to, —O and —N—OR$^5$, wherein R$^5$ is a member selected from the group consisting of hydrogen and alkyl.

The term "alkyl" is used herein to refer to a branched or unbranched, saturated or unsaturated, monovalent hydrocarbon radical having from 1-12 carbons and, preferably, from 1-6 carbons. When the alkyl group has from 1-6 carbon atoms, it is referred to as a "lower alkyl." Suitable alkyl radicals include, for example, methyl, ethyl, n-propyl, i-propyl, 2-propenyl (or allyl), n-butyl, t-butyl, i-butyl (or 2-methylpropyl), etc. As used herein, the term alkyl encompasses "substituted alkyls." Substituted alkyl refers to alkyl as just described including one or more functional groups such as lower alkyl, aryl, aralkyl, acyl, halogen (i.e., alkylhalos, e.g., CF$_3$), hydroxy (e.g., hydroxymethyl), amino, alkylamino, acylamino, acyloxy, alkoxy (e.g., methoxymethyl), mercapto and the like. These groups may be attached to any carbon atom of the lower alkyl moiety.

The term "alkoxy" is used herein to refer to the —OR group, where R is a lower alkyl, substituted lower alkyl, aryl, substituted aryl, aralkyl or substituted aralkyl. Suitable alkoxy radicals include, for example, methoxy, ethoxy, phenoxy, t-butoxy (e.g., methoxyethoxy, methoxymethoxy, etc.), etc.

The term "acyloxy" is used herein to refer to an organic radical derived from an organic acid by the removal of a hydrogen. The organic radical can be further substituted with one or more functional groups such as alkyl, aryl, aralkyl, acyl, halogen, amino, thiol, hydroxy, alkoxy, etc. An example of such a substituted organic radical is glycinate (e.g., —OC(O)CH$_2$NH$_2$). Suitable acyloxy groups include, for example, acetoxy, i.e., CH$_3$COO—, which is derived from acetic acid, formyloxy, i.e., H.CO.O—, which is derived from formic acid and cypionyloxy, which is derived from 3-cyclopentylpropionic acid.

The term "halogen" is used herein to refer to fluorine, bromine, chlorine and iodine atoms.

The term "hydroxy" is used herein to refer to the group —OH.

The term "acyl" denotes groups —C(O)R, where R is alkyl or substituted alkyl, aryl or substituted aryl as defined herein.

The term "aryl" is used herein to refer to an aromatic substituent that may be a single ring or multiple rings which are fused together, linked covalently, or linked to a common group such as an ethylene or methylene moiety. The aromatic ring(s) may include phenyl, naphthyl, biphenyl, diphenylmethyl, 2,2-diphenyl-1-ethyl, and may contain a heteroatom, such as thienyl, pyridyl and quinoxalyl. The aryl group may also be substituted with halogen atoms, or other groups such as nitro, carboxyl, alkoxy, phenoxy, and the like. Additionally, the aryl group may be attached to other moieties at any position on the aryl radical that would otherwise be occupied by a hydrogen atom (such as 2-pyridyl, 3-pyridyl and 4-pyridyl).

The term "alkyl carbonate" is used herein to refer to the group —OC(O)OR, where R is alkyl, substituted alkyl, aryl, or substituted aryl as defined herein.

The term "S-alkyl" is used herein to refer to the group —SR, where R is lower alkyl or substituted lower alkyl.

The term "IS-acyl" is used herein to refer to a thioester derived from the reaction of a thiol group with an acylating agent. Suitable S-acyls include, for example, S-acetyl, S-propionyl and S-pivaloyl. Those of skill in the art will know that S-acyl refers to such thioesters regardless of their method of preparation.

The terms "N-oxime" and "N-alkyloxime" are used herein to refer to the group —N—OR$^5$, wherein R$^5$ is, for example, hydrogen (N-oxime) or alkyl (N-alkyloxime). Those of skill in the art will know that the oximes can consist of the syn-isomer, the anti-isomer or a mixture of both the syn- and anti-isomers.

Within Formula I, certain embodiments are preferred, namely those in which $R^1$ is —N(CH$_3$)$_2$; those in which $R^2$ is halogen or alkoxy; those in which $R^3$ is acyloxy; those in which $R^4$ is alkyl (e.g., methyl and ethyl); and those is which X is —O or —N—OR$^5$, wherein R$^5$ is hydrogen or alkyl. More particularly, compounds which are preferred are those in which $R^1$ is —N(CH$_3$)$_2$; $R^2$ is halogen; $R^3$ is acyloxy; and $R^4$ is alkyl. Within this embodiment, compounds which are particularly preferred are those in which $R^2$ is F, Br or Cl; and R$^4$ is methyl. Also preferred are compounds in which R$^1$ is —N(CH$_3$)$_2$; R$^2$ is alkyl; R$^3$ is acyloxy; R$^4$ is alkyl; and X is —O. Also preferred are compounds in which R$^1$ is —N(CH$_3$)$_2$; R$^2$ is alkoxy; R$^3$ is acyloxy; R$^4$ is alkyl; and X is —O. Within this embodiment, compounds which are particularly preferred are those in which R$^2$ is methoxy or ethoxy; and R$^3$ is acetoxy. Also preferred are compounds in which R$^1$ is —N(CH$_3$)$_2$; R$^2$ is hydroxy; R$^3$ is acyloxy; R$^4$ is alkyl; and X is —O. Also preferred are compounds in which R$^1$ is —N(CH$_3$)$_2$; R$^2$ and R$^3$ are both acyloxy; R$^4$ is alkyl; and X is —O. Within this embodiment, compounds which are particularly preferred are those in which R$^2$ and R$^3$ are both acetoxy. Also preferred are compounds in which R$^1$ is —N(CH$_3$)$_2$; R$^2$ is S-acyl; R$^3$ is hydroxy or acyloxy; R$^4$ is alkyl; and X is —O. Also preferred are compounds in which R$^1$ is —N(CH$_3$)$_2$; R$^2$ is cypionyloxy; R$^3$ is acetoxy; R$^4$ is alkyl; and X is —O. Also preferred are compounds in which R$^1$ is —N(CH$_3$)$_2$; R$^2$ is methoxy; R$^3$ is acetoxy; R$^4$ is alkyl; and X is —N—OR$^5$, wherein R$^5$ is, for example, hydrogen or alkyl (e.g., methyl, ethyl, etc.). Also preferred are compounds in which R$^1$ is —N(CH$_3$)$_2$; R$^2$ and R$^3$ are both acetoxy; R$^4$ is alkyl; and X is —N—OR$^5$, wherein R$^5$ is, for example, hydrogen or alkyl (e.g., methyl, ethyl, etc.).

Specific preferred compounds include, but are not limited to, 17α-acetoxy-21-fluoro-11β-(4-N,N-dimethylaminophenyl)-19-norpregna-4,9-diene-3,20-dione, 17α-acetoxy-21-chloro-11β-(4-N,N-dimethylaminophenyl)-19-norpregna-4,9-diene-3,20-dione, 17α-acetoxy-21-bromoro-11β-(4-N,N-dimethylaminophenyl)-19-nor-pregna-4,9-diene-3,20-dione, 17α,21-diacetoxy-11β-(4-N,N-dimethylaminophenyl)-19-norpregna-4,9-diene-3,20-dione, 17α-hydroxy-21-acetylthio-11β-(4-N,N-dimethylaminophenyl)-19-norpregna-4,9-diene-3,20-dione, 17α-acetoxy-21-acetylthio-11β-(4-N,N-dimethylaminophenyl)-19-norpregna-4,9-diene-3,20-dione, 17α-acetoxy-21-ethoxy-11β-(-4-N,N-dimethylaminophenyl)-19-norpregna-4,9-diene-3,20-dione, 17α-acetoxy-21-methyl-11β-(4-N,N-dimethylaminophenyl)-19-norpregna-4,9-diene-3,20-dione, 17-acetoxy-21-methoxy-11β-(4-N,N-dimethylaminophenyl)-19-norpregna-4,9-diene-3,20-dione, 17α-acetoxy-21-ethoxy-11β-(4-N,N-dimethylaminophenyl)-19-norpregna-4,9-diene-3,20-dione, 17α-acetoxy-21-(3'-cyclopentylpropionyloxy)-11β-(4-N,N-dimethylaminophenyl)-19-norpregna-4,9-diene-3,20-dione, 17α-acetoxy-21-hydroxy-11β-(4-N,N-dimethylaminophenyl)-19-norpregna-4,9-diene-3,20-dione, 17α,21-diacetoxy-11β-(4-N,N-dimethylaminophenyl)-19-norpregna-4,9-diene-3,20-dione3-oxime, and 17α-acetoxy-21-methoxy-11β-(4-N,N-dimethylaminophenyl)-19-norpregna-4,9-diene-3,20-dione3-oxime. Methods for making these compounds are disclosed in U.S. Publication no. 20020025951 A1.

In some embodiments of the present invention, the sustained release compositions are in the form of intravaginal or vaginal rings. These rings are annularly shaped articles made of inert elastomeric materials that can be introduced into the vagina in a simple manner without medical assistance. The ring fits between the rear wall of the vagina and the upper edge of the pubic bone. Numerous types of vaginal rings have been described in the patent and non-patent literature alike. See, e.g., U.S. Pat. Nos. 4,012,496 and 4,155,991 (both to Schopflin et al.); U.S. Pat. No. 4,292,965 (Nash) (which teaches three-layered rings); U.S. Pat. No. 3,545,439 (Duncan); U.S. Pat. No. 3,920,805 (Roseman); U.S. Pat. Nos. 3,991,760 and 3,995,634 (both to Drobish et al.); U.S. Pat. No. 3,995,633 (Gougen); U.S. Pat. Nos. 4,250,611 and 4,286,587 (both to Wong); U.S. Pat. No. 4,596,576 (de Nijs); WO95/00199 (Lehtinen et al.); NL 8500-470-A; and Apter, et al., Contraception 42:285-295 (1990); Burton, et al., Contraception 17:221-230 (1978); Burton et al., contraception 19:507-516 (1979); Jackanicz, Contraception 24:323-339 (1981); Sivin, et al., Contraception 24:341-358 (1981); Timmer, et al., Contraception 43:629-642 (1990); Toivonen, Contraception 20:511-518 (1979); and Sitruk-Ware, et al., Contemporary Clin. Gynecol. & Obstet. 2:287-98 (2002).

Figure 1A:
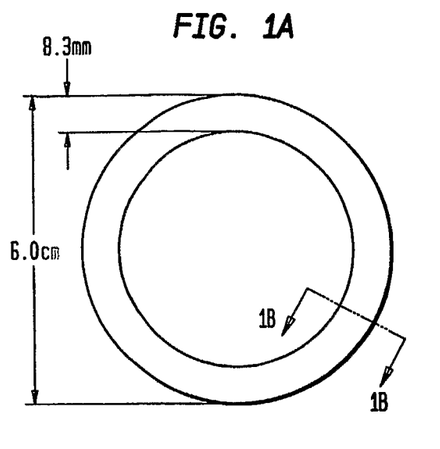
FIG. 1A is a schematic diagram and FIG. 1B is a cross-sectional view of an embodiment of a vaginal ring of the present invention.
Figure 1B:
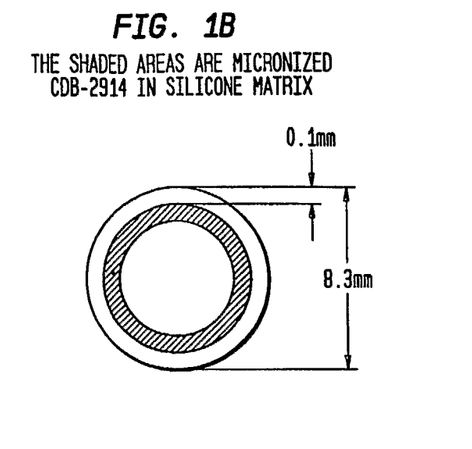
Figure 2A:
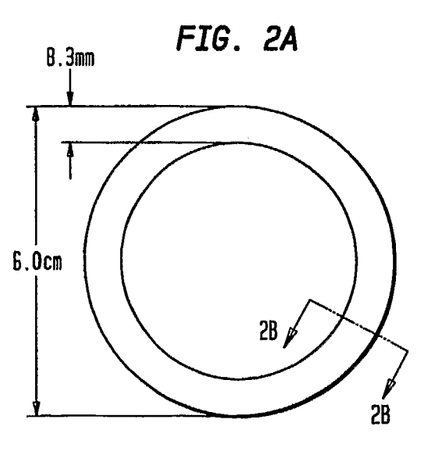
FIG. 2A is a schematic diagram and FIG. 2B is a cross-sectional view of another embodiment of a vaginal ring of the present invention.
Figure 2B:
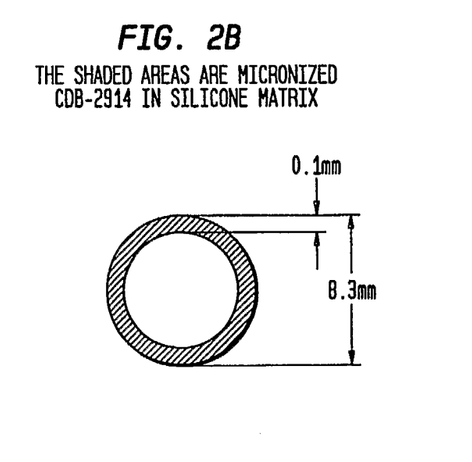

Many basic ring designs are known in the art, e.g., the homogeneous ring, two-layered rings, the Roseman ring and three-layered rings. See, e.g., Weiner et al., Acta Obstet. Gynecol. Scand, Suppl. 54, 1977 p. 35; U.S. Pat. No. 3,920,805 to Roseman and U.S. Pat. No. 4,012,496 to Schopflen. The polymeric materials, e.g., polymers and resins, are physiologically acceptable and inert, as those terms are generally understood by persons in the art. In the homogeneous ring, the contraceptive agent is substantially uniformly dispersed throughout an inert elastomer matrix. See, e.g., U.S. Pat. No. 3,545,439 to Duncan and Victor, et al., Contraception 12:261, 1975. Two-layered rings, as shown schematically in FIGS. 2A and B, contain a polymeric material e.g., an elastomer ring encircled by a second ring of inert physiologically acceptable synthetic resin or elastomer containing (e.g., impregnated with or having dispersed therein so as to form a matrix) a contraceptive agent. See, e.g., U.S. Pat. No. 4,012,496 to Schoepflin, et al. In the Roseman ring, a thin layer of an inert elastomer containing a contraceptive agent is molded onto a central inert core of elastomer. Three-layered rings, as schematically shown in FIGS. 1A and B, contain a layer of an inert elastomer containing a contraceptive agent that surrounds a central inert core of synthetic elastomer, which in turn is surrounded by an outer layer of inert elastomer of variable thickness to control the release rate of the contraceptive agent. Yet another vaginal ring design is taught in U.S. Pat. No. 5,972,372. This patent teaches a vaginal ring which contains a vaginal ring body of a first polymeric material having at least one hollow internal channel defining an opening to the exterior of said body and which channel is adapted to receive a core containing an intravaginally administrable drug through the opening, and a core positioned in the channel, wherein the core contains a pharmaceutically effective amount of at least one intravaginally administrable drug dispersed in the second polymeric material. The first and second polymeric materials may be the same or different. The '372 patent also contains illustrations of shell rings, homogeneous rings, and core rings (a ring having at least two non-extensive cores, each of which may contain the same or different active agents). Preferred vaginal rings for use in the present invention are two-layered and three-layered rings.

Aside from the general structure of the ring, Applicants have also discovered that not all polymeric materials normally used to make rings will provide for acceptable release rates of drugs especially PRMs such as CDB-2914 and closely related structural derivatives. As illustrated in the examples, Applicants unexpectedly discovered that CDB-2914 exhibited a higher release rate from silicone elastomer than another PRM, mifepristone. A variety of physiologically acceptable resins or elastomers have been disclosed in the literature as being suitable for making vaginal rings, including silicone elastomers such as polyorganosiloxanes, e.g., polydimethylsiloxane or a copolymer of dimethylsiloxane and methylvinylsiloxane, conventional silicone rubber, polyurethanes, SILASTIC 382 (Dow Corning), latex rubber, polyamides, polyesters, polytetrafluoroethylene, polyethylene vinyl acetate and nylon. The vaginal rings of the present invention preferably contain silicone elastomers, and more preferably silicone rubbers such as medical grade organopolysiloxanes, such as among the following:

1. Thermosetting organopolysiloxanes to be vulcanized with peroxide curing catalysts, e.g. benzoyl peroxide or di-p-chlorobenzoyl peroxide at temperatures of about 200.degree. C. and requiring a heat after-treatment, e.g. those described in U.S. Pat. Nos. 2,541,137; 2,723,966; 2,863,846; 2,890,188 and 3,022,951.
2. Hydroxyl-terminated organopolysiloxanes of the RTV (room temperature vulcanizing) type which harden to elastomers at room temperature after the addition of cross-linking agents in the presence of curing catalysts and under the atmospheric humidity. Typical curing catalysts are metallic salts of carboxylic acids, preferably tin salts, e.g. tin (II) octoate and tin (II)-2-ethylhexanoate.
3. Single-component silicone rubber compositions which are cured at room temperature under atmospheric humidity without any further additives. These single component compositions contain primarily organopolysiloxanes with two terminal-positioned hydrolyzable acyloxy groups, e.g. acetoxy; the acyloxy groups are hydrolyzed under atmospheric humidity to form trifunctional siloxane units which crosslink the polymer into a cured elastomer. Such organopolysiloxanes are described, e.g., in U.S. Pat. Nos. 2,927,907 and 3,035,016 and in British Patents 798,669 and 804,199.
4. Two-component dimethylpolysiloxane compositions, platinum-catalyzed at room temperature or under slightly elevated temperature and capable of addition cross-linking. The medicated layer can be constructed from an elastomer selected from classes 2 and 3 above and the outer layer can be constructed from an elastomer selected from classes 1 to 4 above, provided the elastomers in class 1 are cured before coming in contact with the medicated layer. The preferred elastomers for use in the core, medicated layer and the outer layer are polydimethylsiloxanes.

The amount of the progesterone receptor modulator present in the sustained release composition typically depends on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those of skill in the art.

The progesterone receptor modulator e.g., CDB-2914, is present in the vaginal ring in amounts effective to allow for the daily release of a therapeutic or contraceptive effective amount of drug. This occurs via diffusion of the drug from the ring into the vaginal vault, and the surrounding tissues. Aside from the considerations mentioned above, in the case of vaginal rings, the amount of drug depends on such factors as the dimensions of the ring, the duration of administration (i.e., the amount of time the ring is intended to remain in the vagina), the solubility of the drug in the ring elastomer, the surface area of the drug reservoir, the distance the drug must diffuse through the ring body to reach its surface and the molecular weight of the drug, and the amount of drug that needs to be released from the ring on a daily basis to achieve the intended effect. For long term contraceptive purposes, the amount is generally in the range of about 400 µg to about 3000 µg per day, and more typically about 1500 µg to about 2500 µg per day. In more preferred embodiments, the amount released is about 2 mg. Amounts less than 400 µg and greater than 3000 µg may also be useful, however. Vaginal rings may be designed to contain enough drug to provide effective contraception for periods of time typically ranging from one month up to about 1 year. In some embodiments, the ring contains enough drug to provide a contraceptive effect for about 3 months. Given these criteria, amounts of drug contained in the vaginal ring generally vary from about 0.2 to about 6 grams, and preferably from about 1 to about 4 grams. For example, a ring intended to remain in the vagina for one year will typically contain about 2 grams of drug.

The dimensions of the vaginal rings can be determined by persons skilled in the art using standard techniques. In general, the vaginal ring typically has an overall diameter of about 40 mm to about 70 mm, preferably from 50 mm to 65 mm, and more preferably about 58 mm. The overall cross sectional diameter of the ring generally ranges from about 2 mm to about 10 mm, and preferably about 6 to 8 mm, and more preferably about 4 to about 8 mm. Thus, the thickness of the inert core generally ranges from about 1 mm to about 9 mm; the thickness of the drug-containing layer generally ranges from about 0.5 mm to about 2.0 mm; and in the case of three-layered rings, the thickness of the outer layer generally ranges from about 0.05 mm to about 0.6 mm, preferably about 0.1 mm to about 0.3 mm. The thickness of the outer layer affects the distance the drug must travel to reach the vaginal tissues. Thus, it can be varied to control the release rate of the drug.

In preferred embodiments wherein the composition is being used for long-term, continuous contraceptive purposes, the contraceptive drug e.g., CDB-2914, is the only active agent in the ring. Thus, in preferred embodiments, the ring does not contain other active agents such as androgens, selective androgen receptor modulators, estrogens or selective estrogen receptor modulators. On the other hand, inert additives may also be present. For example, the structural integrity of the ring may be enhanced by the addition of a particulate material such as fumed silica or diatomaceous earth.

The vaginal rings of the present invention may be prepared in accordance with standard techniques. For example, methods of preparing vaginal rings are described in U.S. Pat. No. 4,292,965. In some embodiments, the ring is prepared first by mixing or dispersing the drug in the elastomer, e.g., to form a matrix. Once the drug is mixed with the matrix material to achieve a substantially uniform dispersion, the desired shape of the resultant dispersion is achieved by molding, casting, extrusion, or other appropriate process. In the case of a three-layered ring, for example, the dispersion may be filled into a rubber tube (e.g., silicone) containing an elastomeric core, followed by joining the two ends of the tube to form a ring. Another method involves co-extrusion. In these embodiments, the layers of elastomer, one of which contains the drug, are co-extruded and then cured by heating at a temperature below the melting point of the drug. Suitable medical adhesives include medical grade Silicone Type A.

The compositions of the present invention may also take the form of a non-vaginal ring sustained release composition, e.g., creams, gels, jellies, foams and suppositories (e.g., effervescent suppositories) that will provide a sustained release of the progesterone receptor modulator, e.g., CDB-2914. Each of these compositions will contain at least one pharmaceutically acceptable excipient, carrier or diluent. Persons skilled in the art may select appropriate ones to make the various types of sustained-release compositions e.g., by resort to standard texts in the art. For example, a vaginal cream according to the invention may contain a hydrocarbon base (e.g. white petrolatum), a solvent (e.g. glycerin or propylene glycol) and an emulsifier (e.g. cetyl alcohol, stearyl alcohol, sodium lauryl sulphate). A vaginal jelly may contain a solvent (e.g. glycerin or propylene glycol) a gel forming agent (e.g. sodium alginate (especially with calcium ions), tragacanth, gelatin, methyl cellulose, sodium carboxymethylcellulose, carbomer and polyvinyl alcohol) and a non-spermicidal or non-sperm-immobilising preservative. Vaginal foam may contain a fluorinated hydrocarbon propellant and a surfactant or emulsifier. Numerous examples of these types of compositions are known in the art. See, e.g., WO 03/093,322, and U.S. Pat. Nos. 5,595,980; 4,585,647; 4,368,186; 5,766,681; 6,207,696; 4,310,510; and 4,795,761. These compositions may further contain one or more other active agents, e.g., a spermicide.

Vaginal gels are preferred. Performance of a gel depends on such factors as solubility of the active agent, selection of enhancer and gelling components and stability of the resultant formulation. Alcohols should be avoided. Although the progesterone receptor modulators, particularly CDB-2914, are not water soluble, they can be formulated in a water-soluble stable complex in cyclodextrins. Gelling agents include hydroxylpropylmethylcellulose, carbopol, and carboxymethyl cellulose. The compositions may further include a pH-adjusting agent in an amount to make the formulation compatible with the vaginal environment. In general, formulations having a pH of about 5 to about 6 are suitable for vaginal administration.

Transdermal gels typically contain aside from the PRM, one or more gelling agents such as carbopols, methyl cellulose, carboxymethyl cellulose, hydroxypropylmethyl cellulose, one or more organic solvents, such as ethyl alcohol, isopropyl alcohol, propylene glycol, glycerol, and one or more penetration enhancers such as dimethyl sulfoxide, urea and its derivatives, surfactants (e.g., sucrose monolaurate, glycerol monooleate, glycerol monolaurate, propylene glycol laurate, and neopentyl glycol dicaprate), polyols, bile salts and derivative, fatty acid and derivatives, azone and liposomes. Transdermal gels may be applied to the skin directly or by way of a patch, also known as a transdermal patch or transdermal therapeutic system. Numerous transdermal patches are known in the art. They may contain, for example, a backing layer substantially impervious to the PRM); an active-substance-containing reservoir, which may be formed of a polymer, which is in contact with e.g., bonded to the backing layer and an adhesive means e.g., pressure sensitive adhesive, which adheres the dosage unit in intimate contact with the skin of the subject being treated to permit the PRM to be absorbed transdermally. They may also contain a removable protective layer. See, e.g., U.S. Pat. Nos. 4,788,062; 4,818,540; 6,207,696; 6,476,029; and 6,521,250.

The amounts of progesterone receptor modulator e.g., CDB-2914, in these sustained release compositions generally varies from 0.2 g to about 6 g. Administration of the sustained release composition will vary e.g., as per the many considerations given above, and particularly the length of time a contraceptive or therapeutic effect is intended. In general, the vaginally administered sustained release compositions are administered once daily and once every 3 to 7 days for transdermal patches.

As in the case of the vaginal rings, when the other sustained release compositions of the present invention are used for contraceptive purposes, it is preferred that the PRM, e.g., CDB-2914, is the only active agent in the ring. Thus, it is preferred that they do not contain other active agents such as androgens, selective androgen receptor modulators, estrogens or selective estrogen receptor modulators. On the other hand, in these as well as any embodiment, inert, pharmaceutically acceptable additives may also be present.

The invention will now be illustrated by way of the following examples. They are not intended to limit the scope of the presently disclosed invention in any way. Unless indicated otherwise, all parts are by weight.

Example 1

Preparation of Rings

The three-layered ring was prepared by inserting an inert silicone tube (with no active agent) into an outer silicone tube. A mixture of CDB-2914 and silicone elastomer was injected into the space between inert core and outer membrane. Upon polymerization of the silicone matrix containing the CDB-2914, the two ends of the tube were joined together with medical grade silicone adhesive to form the ring.

Example 2

In vitro Release Rate of CDB-2914 from the Three-Layered Rings

Figure 3:
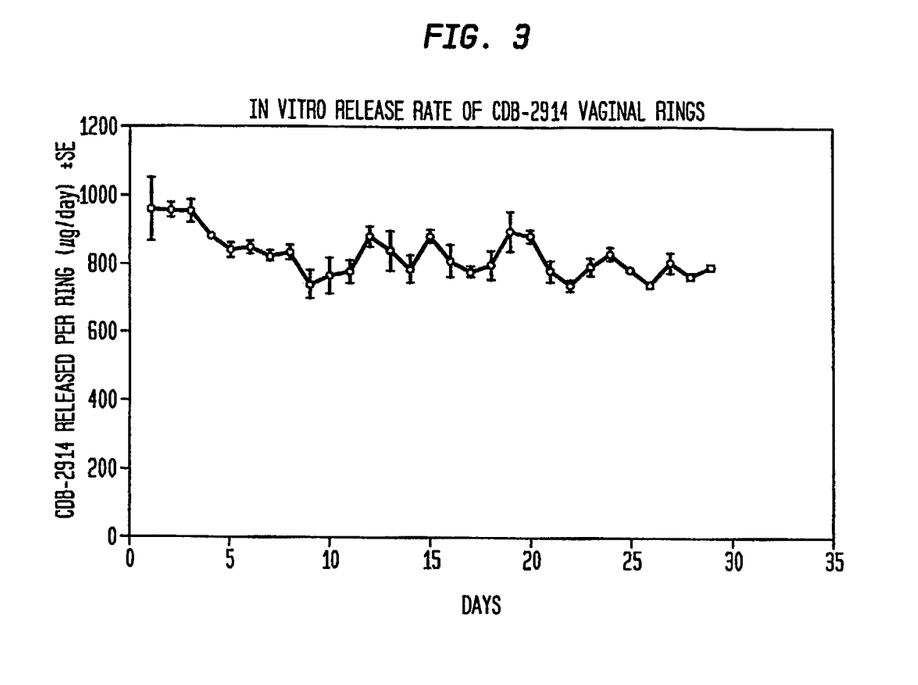
FIG. 3 is a graph showing in vitro release rate of CDB-2914 from a shell vaginal ring of the present invention.

Thread was used to suspend the rings prepared in example 1 individually in 500 mL wide mouth polyethylene bottles with screw caps. 400 mL of redistilled water was added, and the bottles were placed in a shaking water bath at 37 C. The bath was set to make 100 one-inch strokes per minute. The bathing solution was changed every 24 hours. The CDB-2914 concentration in the aqueous medium was measured via HPLC to determine the release rate of CDB-2914. The in vitro release rate of CDB-2914 is graphically shown in FIG. 3.

Example 3

Figure 4:
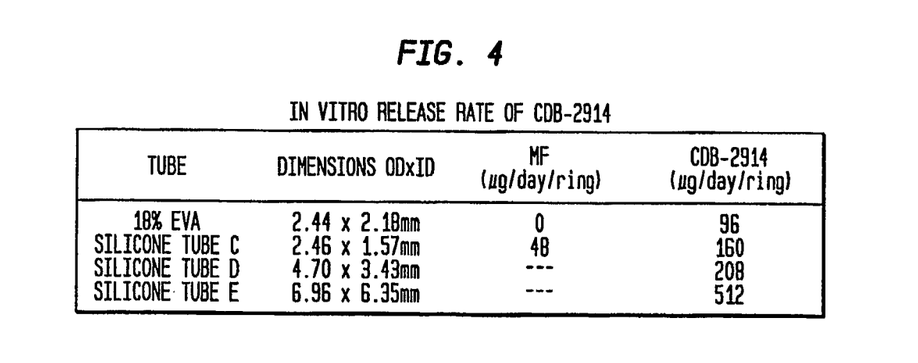
FIG. 4 is a table comparing in vitro release rates of CDB-2914 and mifepristone (MF) from various vaginal rings of the present invention.

Comparative Release Rates of CDB-2914 and Mifepristone from Various Vaginal Rings of the Present Invention Using the same in vitro release rate analysis, vaginal rings were prepared containing either CDB-2914 (20% load, W/W) or mifepristone (20% load, W/W) with several different diameters of silicone tubes, and with tubes containing 18% ethylene vinyl acetate (EVA) as a rate-limiting layer. The rings were prepared by mixing CDB-2914 in a silicone elastomer matrix that was filled into a silicone tube. Upon polymerization, tube was cut into a 16 cm length and the two ends were joined with medical adhesive to form a ring. This vaginal ring has an inner layer of silicone rubber and active agent, and an outer, rate limiting layer. With a silicone tube containing 18% EVA, CDB-2914 was released at the rate of about 96 µg/ring/day, whereas the release of mifepristone was negligible. Using silicone tube C, CDB-2914 was diffused out at more than a 3-fold higher rate than mifepristone (160 µg/ring/day vs. 48 µg/ring/day). Experiments were also conducted using rings made of silicone tube D and silicone tube E. The results are shown in the table in FIG. 4. They show that notwithstanding structural similarities between CDB-2914 and mifepristone (e.g., as illustrated in Stratton, et al., Human Reproduction 15(5):1092-99 (2000)), CDB-2914 exhibited an unexpectedly higher release rate from silicone-based vaginal rings. The results also show that the use of EVA as a rate-limiting polymer in vaginal rings of the present invention is less preferred than silicone elastomers.

Example 4

In Vivo Use of Vaginal Rings of the Present Invention in Women

Figure 5A:
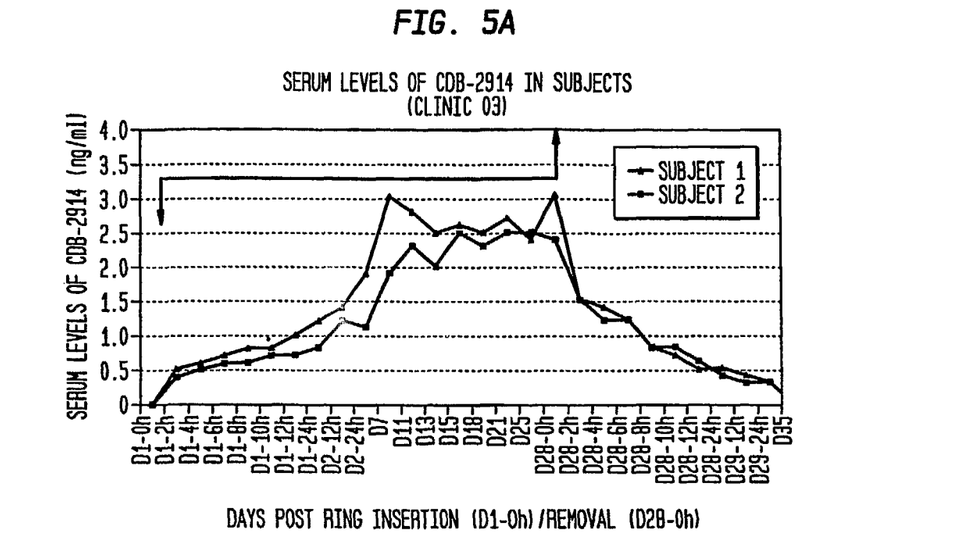
FIGS. 5A and B are graphs showing serum levels of CDB-2914 (released from vaginal rings) in women.
Figure 5B:
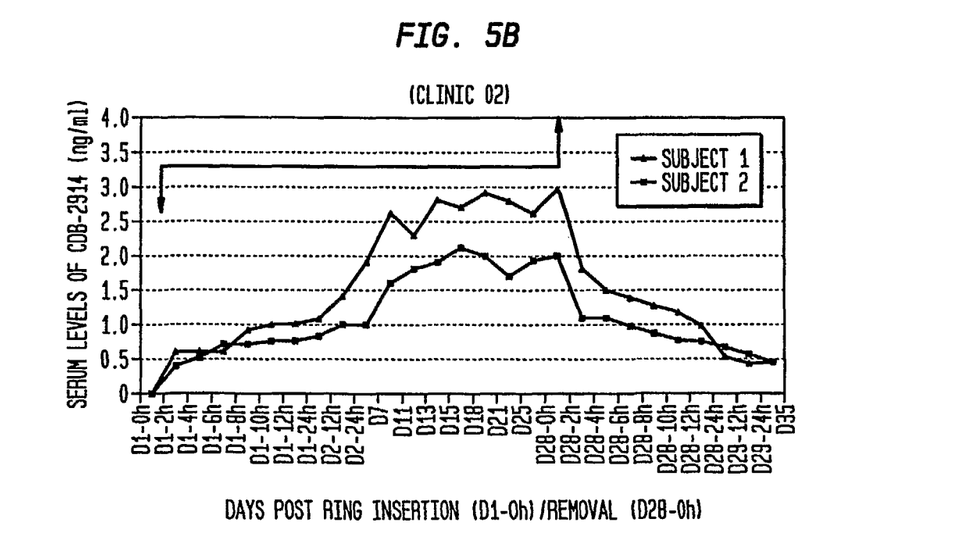
Figure 6:
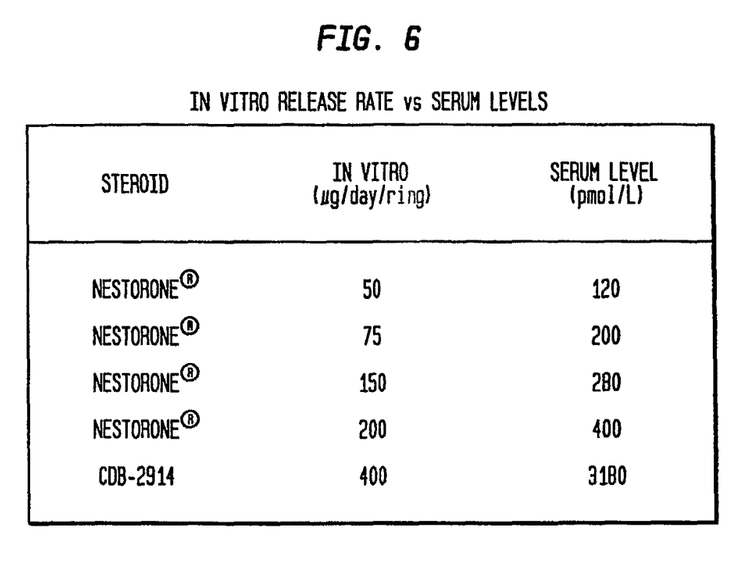
FIG. 6 is a table showing comparative in vitro release rates and serum levels of CDB-2914 and Nestorone® (NES).

A pharmacokinetic study was conducted abroad in two clinics. Radioimmunoassay and liquid chromatography/mass spectroscopic method (LC/MS) were used to measure the serum levels of CDB-2914 and its immunoreactive metabolites. The results of two methods were comparable. After insertion of the ring into the subjects, CDB-2914 was absorbed into the blood stream, increased continuously and reached a plateau at approximately 7 days post-insertion (2-3 ng/mL). Serum levels decreased upon removal of ring at Day 29 (See FIGS. 5A and 5B). No bursting release of CDB-2914 was observed immediately after insertion of the rings. As compared to Nestorone® (NES), a synthetic progestin, CDB-2914 was absorbed more readily into the blood stream, and the serum concentration of CDB-2914 was higher than that of Nestorone (see FIG. 6).

All patent and non-patent publications cited in this specification are indicative of the level of skill of those skilled in the art to which this invention pertains. All these publications and patent applications are herein incorporated by reference to the same extent as if each individual publication or patent application was specifically and individually indicated as being incorporated by reference herein.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A vaginal ring composition comprising a synthetic polymer having contained therein a contraceptively effective amount of a steroid comprising a progesterone receptor modulator (PRM), with the proviso that the progesterone receptor modulator is not an androgen, selected androgen receptor modulator, estrogen, or selected estrogen receptor modulator.

2. The vaginal ring of claim 1, wherein said polymer comprises a silicone elastomer.

3. The vaginal ring of claim 1, further comprising a layer of a silicone elastomer overlying said polymer.

4. The vaginal ring of claim 1, further comprising a polymer core, which is surrounded by an outer layer comprising the polymer and the PRM.

5. The vaginal ring of claim 4, further comprising an outer polymer layer surrounding the layer comprising the polymer and wherein said PRM comprises 17α-acetoxy-11β-(4-N,N-dimethylaminophenyl)-19-norpregna-4,9-diene-3,20-dione (CDB-2914).

6. The vaginal ring of claim 4, wherein the polymer comprises a silicone elastomer.

7. The vaginal ring of claim 4, wherein the polymer core and the outer layer each comprise silicone elastomers, which may be the same or different.

8. The vaginal ring of claim 7, wherein the silicone elastomer in the core comprises a polydimethylsiloxane, and the silicone elastomer in the outer layer comprises a polydimethylsiloxane.

9. The vaginal ring of claim 1, wherein said PRM comprises a 21-substituted progesterone derivative represented by the following formula:

wherein R⁴ is a functional group selected from the group consisting of —OCH₃, —SCH₃, —N(CH₃)₂, —NHCH₃, —CHO, —COCH₃ and —CHOHCH₃; R² is a functional group selected from the group consisting of halogen, alkyl, acyl, hydroxy, alkoxy, acyloxy, alkyl carbonate, cypionyloxy, S-alkyl and S-acyl; R³ is a functional group selected from the group consisting of alkyl, hydroxy, alkoxy and acyloxy; R⁴ is a functional group selected from the group consisting of hydrogen and alkyl; and X represents —O and —N—OR⁵, wherein R⁵ is hydrogen or an alkyl group.

10. The vaginal ring of claim 1, wherein said PRM comprises 17α-acetoxy-11β-(4-N,N-dimethylaminophenyl)-19-norpregna-4,9-diene-3,20-dione (CDB-2914), or a metabolite thereof selected from the group consisting of monodemethylated CDB-2914 and didemethylated CDB-2914.

11. The vaginal ring of claim 1, wherein the amount of said PRM is about 0.2 grams to about 6 grams.

12. The vaginal ring of claim 1, wherein the amount of said PRM is about 1 to about 4 grams.

13. The vaginal ring of claim 1, wherein the amount of said PRM is about 2 grams.

14. A method of long-term contraception, comprising administration of a vaginal ring comprising a synthetic polymer and an effective amount of a steroid consisting essentially of a PRM, with the proviso that the progesterone receptor modulator is not an androgen, selected androgen receptor modulator, estrogen, or selected estrogen receptor modulator.

15. The method of claim 14, wherein the amount of the PRM is effective to provide a contraceptive effect for about 1 month.

16. The method of claim 14, wherein the amount of the PRM is effective to provide a contraceptive effect for about 3 months.

17. The method of claim 14, wherein the amount of the PRM is effective to provide a contraceptive effect for about 1 year.

18. The method of claim 14, wherein the PRM is CDB-2914, or a metabolite thereof selected from the group consisting of monodemethylated CDB-2914 and didemethylated CDB-2914.

* * * * *

UNITED STATES PATENT AND TRADEMARK OFFICE
CERTIFICATE OF CORRECTION

| | |
|---|---|
| PATENT NO. | : 8,865,200 B2 |
| APPLICATION NO. | : 11/631877 |
| DATED | : October 21, 2014 |
| INVENTOR(S) | : Regine Sitruk-Ware and Yun-Yen Tsong |

Page 1 of 1

It is certified that error appears in the above-identified patent and that said Letters Patent is hereby corrected as shown below:

On the title page item (73), line 2, "Assignee:" insert -- The Population Council, Inc. and --.

Signed and Sealed this
Twenty-eighth Day of June, 2016

Michelle K. Lee
*Director of the United States Patent and Trademark Office*